(12) United States Patent
Maraschino

(10) Patent No.: US 6,407,300 B2
(45) Date of Patent: Jun. 18, 2002

(54) APPARATUS AND PROCESS FOR HYDROGENATIONS

(75) Inventor: Mario J. Maraschino, Houston, TX (US)

(73) Assignee: Catalytic Distillation Technologies, Pasadena, TX (US)

( * ) Notice: Subject to any disclaimer, the term of this patent is extended or adjusted under 35 U.S.C. 154(b) by 0 days.

(21) Appl. No.: 09/833,294

(22) Filed: Apr. 11, 2001

Related U.S. Application Data

(62) Division of application No. 09/262,251, filed on Mar. 4, 1999, now Pat. No. 6,284,104.

(51) Int. Cl.$^7$ .............................. C07C 7/167; C07C 5/08
(52) U.S. Cl. ..................... 585/259; 585/258; 585/265; 203/DIG. 6
(58) Field of Search .................... 585/258, 259, 585/265; 203/DIG. 6

(56) References Cited

U.S. PATENT DOCUMENTS

| | | | |
|---|---|---|---|
| 4,215,011 A | 7/1980 | Smith, Jr. | 422/211 |
| 4,443,559 A | 4/1984 | Smith, Jr. | 502/527 |
| 4,950,834 A | 8/1990 | Arganbright et al. | 585/440 |
| 5,308,592 A | 5/1994 | Yang et al. | |
| 5,321,163 A | 6/1994 | Hickey et al. | 568/54 |
| 5,595,634 A | 1/1997 | Hearn et al. | 203/29 |
| 5,599,997 A | 2/1997 | Hearn et al. | 564/450 |
| 5,628,880 A | 5/1997 | Hearn et al. | 203/29 |
| 5,773,670 A | 6/1998 | Gildert et al. | 585/266 |
| 5,925,799 A | * 7/1999 | Stanley et al. | 585/259 |

FOREIGN PATENT DOCUMENTS

| | | |
|---|---|---|
| EP | 0 556 025 A1 | 8/1993 |
| GB | 835 689 | 5/1960 |
| GB | 920 012 | 3/1963 |

OTHER PUBLICATIONS

Boitiaux, et al, Newest Hydrogenation Catalysts, *Hydrocarbon Processing*, Mar. 1985 pp 51–59.

Derrien, et al "The IFP Selective Hydrogenation Process" *Chemical Engineering Progress*, Jan. 1974 pp 74–80.

* cited by examiner

Primary Examiner—Thuan D. Dang
(74) Attorney, Agent, or Firm—Kenneth H. Johnson

(57) ABSTRACT

An apparatus and process for treating a complex mixture of hydrocarbons containing undesirable olefinic compounds to remove the mono olefins and diolefins in two stages and separate a desirable key component from the mixture, by first treating the key component in a reactive distillation column under mild conditions to hydrogenate diolefins then separating the diolefin-depleted key component and any lighter materials from the heavier components and sending the diolefin-depleted key component and lighter materials to a second reactive distillation column where the lights are removed overhead and the diolefin-depleted key component is hydrogenated under more severe conditions to remove the mono olefins.

6 Claims, 1 Drawing Sheet

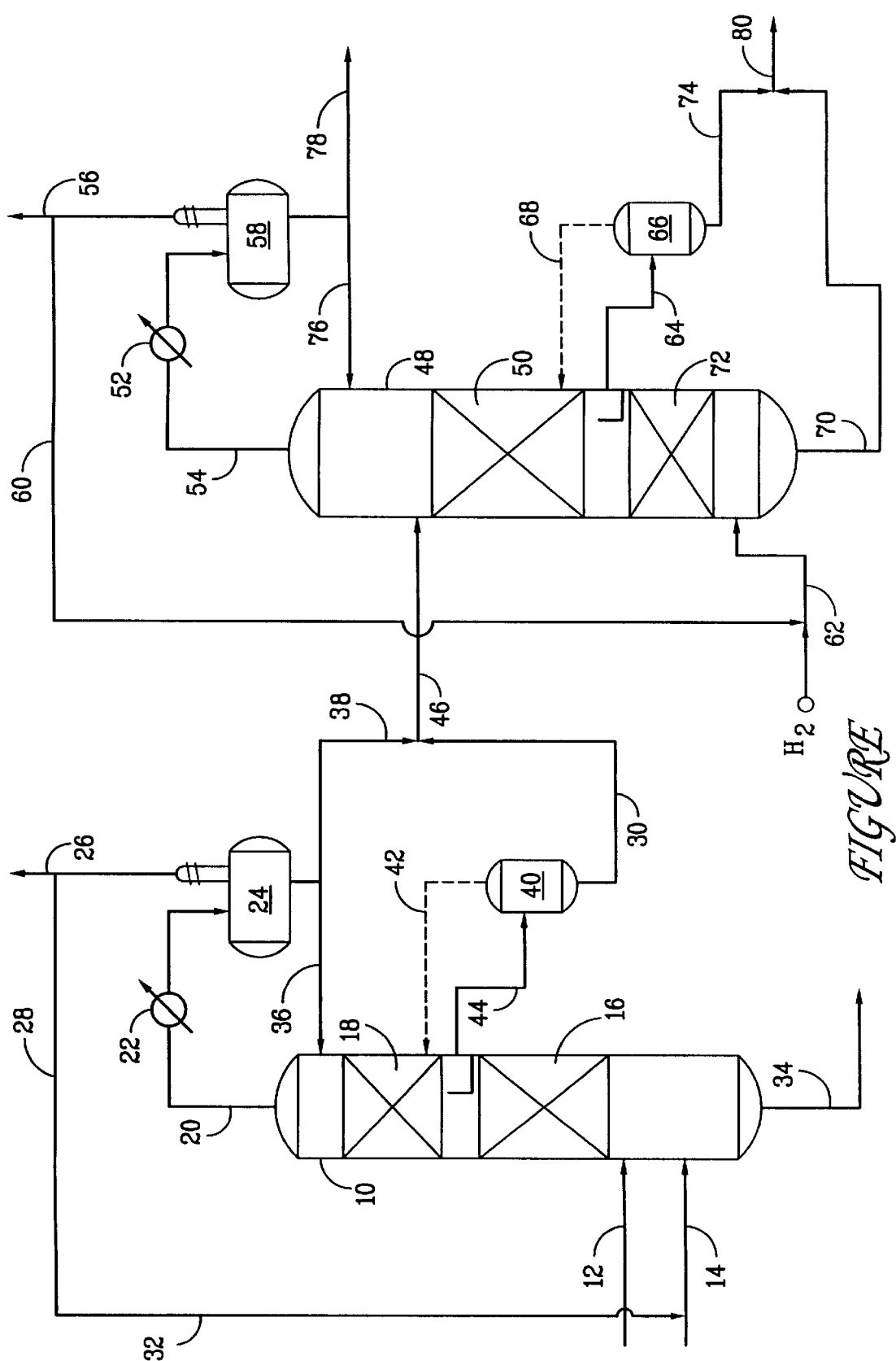
FIGURE

APPARATUS AND PROCESS FOR HYDROGENATIONS

This is a division of application Ser. No. 09/262,251 filed on Mar. 4, 1997, now U.S. Pat. No. 6,284,104.

BACKGROUND OF THE INVENTION

1. Field of the Invention

The present invention relates to an apparatus and process for improving the flexibility of operation of reactive distillation hydrogenation processes.

2. Related Art

The use of catalysts in a distillation column to concurrently carry out chemical reactions and separate the reaction products has been practiced for some time. Surprisingly, this use of a catalytic distillation column reactor lends itself particularly well for hydrogenations. See for example, U.S. Pat. Nos. 5,595,634; 5,599,997; 5,628,880; 5,773,670 and European Patent No. 0556025 B1. The combination is useful because the reactants in the liquid phase are quickly separated from the reaction products due to boiling point differences by fractional distillation. Thus further reaction is suppressed.

Several different arrangements have been disclosed to achieve the desired result. For example, British Patents 2,096,603 and 2,096,604 disclose placing the catalyst on conventional trays within a distillation column. A series of U.S. patents, including those listed above and more, particularly U.S. Pat. Nos. 4,443,559 and 4,215,011 disclose using the catalyst as part of the packing in a packed distillation column. The use of multiple beds in a reaction distillation tower is also known and illustrated, for example, in U.S. Pat. Nos. 4,950,834; 5,321,163; and 5,595,634.

In reactive distillations, such as catalytic distillation, as in any other distillation, there is no rigid cut off between the components. Reactions carried on in specified portions of the column using some constituents may leave undone other desirable treatment of other portions of the column constituents.

For example, mixed refinery streams often contain a broad spectrum of olefinic compounds. This is especially true of products from either catalytic cracking or thermal cracking processes (pyrolysis gas). These unsaturated compounds comprise ethylene, acetylene, propylene, propadiene, methyl acetylene, butenes, butadiene, amylenes, hexenes, etc. Many of these compounds are valuable especially as feed stocks for chemical products. Olefins having more than one double bond and the acetylenic compounds (having a triple bond) have lesser uses and are detrimental to many of the chemical processes in which the single double bond compounds are used, for example, polymerization. Sulfur and nitrogen compounds, among others, are frequently desirably removed also and they may be effectively removed from a portion of the column constituents, but because of different boiling points for other portions of the column constituents and the contaminants therein, not all of the contaminants may be removed.

Generally it is more difficult to remove both dienes and olefins than dienes alone. Diene-rich streams will hydrogenate at a higher volumetric rate under milder conditions than will a diene depleted olefinic stream. Sulfur in the several hundred ppm range is not uncommon for some feeds. Palladium hydrogenation catalysts are not able to handle such high sulfur levels, however, double-digit diene levels often present in these feeds overwhelm the sulfur impurities in their mutual competition for catalyst sites thereby providing reasonable rates notwithstanding.

In hydrotreating streams with high concentrations of dienes present (above 1000 ppm), there is a need to refrain from using high temperatures to avoid oligomerization. Generally, temperatures in the area of 170° F. or above are avoided. Such operating restraints create conditions which are unfavorable for exhaustive olefin conversion in the same unit in which the diene is eliminated.

The present invention provides apparatus and process to address the reactive distillation hydrogenation of feed streams having concentrations of both mono and di-olefins.

SUMMARY OF THE INVENTION

The present invention includes an apparatus for conducting reactive distillations comprising a first distillation column, a first primary catalyst bed for carrying out a hydrogenation of unsaturated compounds comprising diolefins, said first primary catalyst bed being positioned in said distillation column to provide a first reaction zone for diolefins in said first distillation column, and optionally, a first secondary catalyst bed above said first primary catalyst bed, said first secondary catalyst bed to provide a second reaction zone for diolefins remaining in said first distillation column after said first reaction zone, a first mixed saturated/unsaturated compound feed entry below said first primary bed, a hydrogen feed below said primary bed, a bottoms line and an overhead line connecting to a second distillation column comprising a second primary catalyst bed for carrying out hydrogenation of unsaturated compounds comprising mono olefins from said first distillation column, said second primary catalyst bed being positioned in said distillation column to provide a first reaction zone for unsaturated compounds in said second distillation column, and optionally, a second secondary catalyst bed below said second primary bed, said second secondary catalyst bed to provide a second reaction zone for mono olefins remaining in the second distillation column after said first reaction zone, said overhead line from said first distillation column connecting to said second distillation column above said second primary catalyst bed and a hydrogen feed below said second primary bed.

The process carried out in the apparatus is also part of the present invention.

There may be distillation structures or trays between the primary and secondary beds. Hydrogenation reactions liberate a significant heat of reaction (on the order of 50,000 or greater BTU/lb mole $H_2$ consumed). This released heat adds to vapor load in the column. Optionally, side condensers may be used to keep the uniformity of the vapor profile in the column within desired ranges. A secondary catalyst bed may be positioned in the distillation column, above or below the primary bed as heretofore described, to allow lighter or heavier boiling components to be exposed to additional catalyst and be purified or treated further.

The term "reactive distillation" is used to describe the concurrent reaction and fractionation in a column. For the purposes of the present invention, the term "catalytic distillation" includes reactive distillation and any other process of concurrent reaction and fractional distillation in a column regardless of the designation applied thereto.

The catalyst beds as used in the present invention may be described as fixed, meaning positioned in a fixed area of the column and include expanded beds and ebulating beds of catalysts. The catalysts in the beds may all be the same or different so long as they carry out the function of hydrogenation as described. Catalysts prepared as distillation structures are particularly useful in the present invention.

BRIEF DESCRIPTION OF THE DRAWING

The FIGURE is a simplified process flow diagram of one embodiment of the invention.

DETAILED DESCRIPTION OF THE INVENTION

The present invention is particularly useful for removal of mono olefins and diolefins from cracked gas streams. Thermally cracked gas streams have a particularly wide range of carbon numbers and compound types. Normally, compounds in one carbon number range (such as $C_4$'s in a $C_4/C_5$ splitter) will function as the light key grouping in the column. Thus compounds one carbon number greater (such as $C_5$'s in a $C_4/C_5$ splitter) will serve as the heavy key grouping for the column.

Hydrogenation is the reaction of hydrogen with a carbon-carbon multiple bond to "saturate" or partially saturate the compound. This reaction has long been known and is usually done at super atmospheric pressures and moderate temperatures using a large excess of hydrogen over a metal catalyst. Among the metals known to catalyze the hydrogenation reaction are platinum, rhenium, cobalt, molybdenum, nickel, tungsten and palladium. Generally, commercial forms of catalysts use supported oxides of these metals. The oxide is reduced to the active form either prior to use with a reducing agent or during use by the hydrogen in the feed. These metals also catalyze other reactions, most notably dehydrogenation at elevated temperatures. Additionally, they can promote the reaction of olefinic compounds with themselves or other olefins to produce dimers or oligomers as residence time is increased.

Selective hydrogenation of hydrocarbon compounds has been known for quite some time. Peterson et al in "The Selective Hydrogenation of Pyrolysis Gasoline," presented to the Petroleum Division of the American Chemical Society in September of 1962, discusses the selective hydrogenation of $C_4$ and higher diolefins. Boitiaux et al in "Newest Hydrogenation Catalyst", *Hydrocarbon Processing*, March 1985, presents a general overview of various uses of hydrogenation catalysts.

FIRST COLUMN

The first column is operated with the catalyst located above the hydrocarbon feed. It is operated under conditions to reduce only dienes by hydrogenation. The column is operated to move a key component, for example $C_5$, upward into the primary and any secondary beds under conditions of pressure and temperature to hydrogenate only the dienes, e.g., 150° F. to a top temperature of 170–200° F. at 10 to 75 psig. The exact upper temperature will depend on the diene makeup and other unsaturates such as the acetylenes and the stability of the particular mix of unsaturates to oligomerization.

The upflow of the key component operates the paradigm shift that keeps the catalyst clean and inhibits coking of the dienes. The faster reaction rates of the dienes compared to the mono olefins in hydrogenation allow short superficial vapor phase contact times in the range of 20–60 seconds.

The heaviest carbon-range number that is directed upward serves as the light-key carbon range for the column. Compounds of lower carbon number than this behave as the "lighter than light keys" of the system. These lighter compounds tend to equilibrate more into vapor than into liquid which makes reaction for the dienes in that carbon group much more difficult. However, use of a secondary reaction zone with catalyst (above at a lower temperature that the primary bed) allows the concentration of this lower carbon number fraction. Thus, the combined primary bed and the optional upper secondary bed together handle a wider boiling range than would otherwise be achievable.

SECOND COLUMN

The second column revives the diene depleted overhead from the first column and feeds it above the primary and any optional secondary beds where it is hydrogenated in the reactive distillation mode. In the near absence of dienes e.g. <0.1 wt %, higher temperatures in the range of 200–325° F. are used at pressures in the range of 60–150 psig. Mono olefins-only systems tend to have less favorable hydrogen uptake than diene-rich streams. The superficial vapor phase contact time even under the more severe conditions is 50–90 second range. Note that the key component carbon numbers in the second column may be coincident with or separate from the key component carbon numbers in the first column depending on the objectives of the operation.

The key component builds up in the column liquid and favors the reaction on the key component. In contrast the heavier carbon-range fraction thins out in the downflowing liquid. However, inclusion of a bottoms secondary catalyst bed (which is lower in the column where the higher temperature causes more boil up of the heavies) can be used to concentrate the heaviest carbon-number range species and react the heavier olefins out more effectively also. As in any distillation there is a temperature gradient within the distillation column reactor. The temperature at the lower end of the column contains higher boiling material and thus is at a higher temperature than the upper end of the column.

The result of the operation of the process in the distillation column reactor is that lower hydrogen partial pressures (and thus lower total pressures) may be used.

It is believed that the present distillation column reaction is a benefit first, because the reaction is occurring concurrently with distillation and the initial reaction products and other stream components are removed from the reaction zone(s) as quickly as possible reducing the likelihood of side reactions. Second, because all the components are boiling, the temperature of reaction is controlled by the boiling point of the mixture at the system pressure. The heat of reaction simply creates more boil up, but no increase in temperature at a given pressure. As a result, a great deal of control over the rate of reaction and distribution of products can be achieved by regulating the system pressure. A further benefit that this reaction may gain from distillation column reactions is the washing effect, particularly in the downflow operation of the second column that the internal reflux provides to the catalyst thereby reducing polymer build up and coking.

Referring now to the FIGURE, a process flow diagram for the removal of unsaturates, primarily mono- and di-olefins from a full range pyrolysis gas. Such items as reboilers, compressors, pumps and the like have been omitted but their normal utilization is readily apparent to those in the art.

The feed, a pyrolysis gas as described in TABLE 1, enters the first column 10 via line 12.

TABLE 1

| Component | Wt % |
|---|---|
| BD/C4Acetylene | 0.2 |
| Butylenes | 0.1 |
| Butanes | 0.0 |
| C5 Saturates | 1.0 |
| C5 Olefins | 4.2 |
| C5 Diolefins | 13.0 |
| C6 Saturates | 2.7 |
| C6 Olefins | 2.3 |
| C6 Diolefins | 7.0 |
| C7 Saturates | 1.5 |
| C7 Olefins | 1.1 |
| C7 Diolefins | 3.4 |
| C8 Saturates | 0.5 |
| C8 Olefins | 0.4 |
| C8 Diolefins | 1.2 |
| Benzene | 18.7 |
| Toluene | 17.4 |
| EthylBenzene | 2.1 |
| Xylenes | 7.6 |
| Styrene | 2.6 |
| Heavier | 12.9 |
| Total | 100.0 |

In this illustration the tower 10 is operated under conditions to take the $C_6$ fraction upward (bottoms −394° F. top −212° F. at 60 psig.) The $C_7$ and heavier carbon atom components are removed via line 34 for other processing. The $C_6$ fraction contains some $C_7$ and heavier but is comprised of predominantly $C_6$ and lighter carbon number components.

$C_6$ components contain principally alkanes, benzene, 5 to 12% mono olefins and 15 to 35% dienes. Similarly, the lighter components contain a wide distribution of species including dienes and mono olefins. Hydrogen is added via line 14 at a rate to provide an excess stoichiometric amount to the dienes present in the $C_6$ and higher fraction. In bed 16 a hydrogenation catalyst is provided in the form of distillation structure. Under the conditions of temperature and pressure described there is both a vapor and liquid phase comprised principally of the $C_6$ components and as a result the $C_6$ dienes are substantially eliminated.

The higher components under these conditions are principally vaporous in bed 16. However, the temperature in bed 18, also a hydrogenation catalyst as a distillation structure, is lower because of temperature gradient in the column. The secondary bed 18 allows the lower boiling components to undergo the same type of two phase contact as the $C_6$ fraction in bed 16 thereby allowing a concentration of this higher portion with the dienes substantially eliminated. A side draw 44 is used to remove a portion of the lights diene-depleted concentrate and diene-depleted $C_6$ into collector 40. A portion of the collected material can be returned via line 42 (dotted line) to the column 10 to maintain the vapor load on the column. Otherwise the material from side draw 44 is fed to the second column 48 via line 46.

An overhead 20 also containing mostly diene-depleted $C_5$, $C_6$ and lighter material goes through condenser 22 into collector 24. The non-condensibles are removed for recycle to the hydrogen feed 14 or for disposal via line 26. A portion of the condensed material is returned as reflux 36 to column 10 and the remainder fed via 38 to line 46 into column 48.

The feed from column 10 is characterized as having almost all of the diene and greater unsaturates (acetylenes) removed by hydrogenation with little formation of oligomers. The olefins are substantially untouched because of the restricted operating temperature.

In column 48 the operating conditions are more severe in order to hydrogenate the mono olefins (bottoms −338° F., top −251° F. at 100 psig). The feed enters above primary catalyst bed 50 which is a hydrogenation catalyst prepared as a distillation structure. Again, the conditions are such that the key component, the $C_6$ constituents, is moved downward. The lighter components, primarily $C_5+$, exit via overhead line 54 through condenser 52 into collector 58. The non-condensibles are removed either for disposal via line 56 or recycle via line 60 to hydrogen feed 62. A small portion of the liquid in collector 58 is removed via line 78 and the remainder returned via line 76 to column 48 as reflux.

A collector 66 is located on side draw 64 which removes hydrogenated product via line 74. A portion may be returned via line 68 to control the vapor load on the column. Alternatively the side draw stream 64 may be recovered as a vapor (elimination of the collector 66), which, although it will result in an energy penalty, will provide other benefits, namely (a) further retention of the heavy olefins in the secondary bed 72 and (b) a greater increase in the temperature of bed 72 relative to the primary bed 50, both of which enhance the performance of the secondary bed.

Secondary bed 72 contains a hydrogenation catalyst as a distillation structure and any heavier fraction remaining is concentrated and given a polishing hydrogenation and recovered via line 70 for combination with the side draw stream 74 into product stream 80.

Table 2 shows the temperature profile and distribution of the materials in the column 10. The conditions in the secondary catalyst bed 18 (corresponds to trays 4–16) and the primary bed 16 (corresponds to trays 17–30) are represented by the blocked out areas. The other trays are denoted by number. Tray 48 is the reboiler.

TABLE 2

| TRAY | TEMP °F. | PRESSURE PSIA | LIQUID LBM/H | VAPOR LBM/H | FEED LBM/H | PRODUCT LBM/H |
|---|---|---|---|---|---|---|
| 1C | 101.4 | 74.7 | 3510 | | | 290.6 vap. 140.2 liq. |
| 2 | 211.6 | 74.7 | 4912 | 3940 | | |
| 3 | 215.8 | | 4902 | 5343 | | |
| BED | 217.7 | 75.1 | 4851 | 5332 | | |
| 18 | 219.5 | 75.3 | 4794 | 5282 | | |
| | 221.3 | 75.5 | 4730 | 5225 | | |
| | 223.3 | 75.7 | 4658 | 5161 | | |
| | 225.6 | 75.9 | 4577 | 5089 | | |
| | 228.4 | 76.1 | 4485 | 5008 | | |
| | 231.9 | 76.3 | 4385 | 4916 | | |
| | 236.0 | 76.5 | 4278 | 4815 | | |
| | 240.6 | 76.7 | 4170 | 4709 | | |
| | 245.7 | 76.9 | 4064 | 4601 | | |
| | 250.8 | 77.1 | 3962 | 4495 | | |
| | 255.9 | 77.3 | 3863 | 4392 | | |
| | 260.8 | 77.5 | 3266 | 4294 | | 503.8 Liq |
| BED | 265.6 | 77.7 | 3184 | 4201 | | |
| 16 | 269.4 | 77.9 | 3113 | 4118 | | |
| | 272.4 | 78.1 | 3050 | 4047 | | |
| | 274.6 | 78.3 | 2995 | 3985 | | |
| | 276.2 | 78.5 | 2945 | 3930 | | |
| | 277.3 | 78.7 | 2898 | 3879 | | |
| | 278.1 | 78.9 | 2852 | 3832 | | |
| | 278.7 | 79.1 | 2808 | 3787 | | |
| | 279.2 | 79.3 | 2764 | 3743 | | |
| | 279.7 | 79.5 | 2719 | 3698 | | |
| | 280.2 | 79.7 | 2672 | 3653 | | |
| | 281.0 | 79.9 | 2621 | 3606 | | |

TABLE 2-continued

| TRAY | TEMP °F. | PRESSURE PSIA | LIQUID LBM/H | VAPOR LBM/H | FEED LBM/H | PRODUCT LBM/H |
|---|---|---|---|---|---|---|
|  | 282.2 | 80.1 | 2563 | 3555 |  |  |
|  | 284.3 | 80.3 | 2489 | 3497 |  |  |
| 31 | 288.1 | 80.5 | 2376 | 3423 |  |  |
| 32 | 296.2 | 80.7 | 3532 | 3311 | 1206.2 liq. |  |
|  |  |  |  |  | 237.0 vap. |  |
| 33 | 310.2 | 80.9 | 3645 | 3023 |  |  |
| 34 | 315.3 | 81.1 | 3648 | 3136 |  |  |
| 35 | 319.7 | 81.3 | 3645 | 3139 |  |  |
| 36 | 324.1 | 81.5 | 3639 | 3136 |  |  |
| 37 | 328.7 | 81.7 | 3632 | 3131 |  |  |
| 38 | 333.6 | 81.9 | 3626 | 3124 |  |  |
| 39 | 338.7 | 82.1 | 3621 | 3117 |  |  |
| 40 | 343.8 | 82.3 | 3618 | 3112 |  |  |
| 41 | 348.7 | 82.5 | 3616 | 3110 |  |  |
| 42 | 353.2 | 82.7 | 3613 | 3108 |  |  |
| 43 | 357.5 | 82.9 | 3608 | 3105 |  |  |
| 44 | 361.6 | 83.1 | 3597 | 3099 |  |  |
| 45 | 366.1 | 83.3 | 3575 | 3088 |  |  |
| 46 | 371.6 | 83.5 | 3532 | 3066 |  |  |
| 47 | 379.8 | 83.7 | 3450 | 3023 |  |  |
| 48R | 393.5 | 83.9 |  | 2941 |  | 508.7 liq. |

Table 3 shows the temperature profile and distribution of materials in column 48. The conditions in the secondary catalyst bed 72 (corresponds to trays 38–46) and the primary bed 50 (corresponds to trays 19–31) are represented by the blocked out areas. The other trays are denoted by number. Tray 49 is the reboiler.

TABLE 3

| TRAY | TEMP °F. | PRESSURE PSIA | LIQUID LBM/H | VAPOR LBM/H | FEED LBM/H | PRODUCT LBM/H |
|---|---|---|---|---|---|---|
| 1C | 131.2 | 114.7 | 1504 |  |  | 134.1 vap. |
|  |  |  |  |  |  | 208.7 Liq. |
| 2 | 251.1 | 114.7 | 2247 | 1846 |  |  |
| 3 | 255.4 | 114.9 | 2268 | 2590 |  |  |
| 4 | 257.3 | 115.1 | 2265 | 2611 |  |  |
| 5 | 259.0 | 115.3 | 2258 | 2607 |  |  |
| 6 | 260.6 | 115.5 | 2250 | 2601 |  |  |
| 7 | 262.4 | 115.7 | 2240 | 2593 |  |  |
| 8 | 264.3 | 115.9 | 2228 | 2583 |  |  |
| 9 | 266.5 | 116.1 | 2214 | 2570 |  |  |
| 10 | 268.7 | 116.3 | 2198 | 2556 |  |  |
| 11 | 271.2 | 116.5 | 2182 | 2541 |  |  |
| 12 | 273.8 | 116.7 | 2165 | 2525 |  |  |
| 13 | 276.4 | 116.9 | 2149 | 2508 |  |  |
| 14 | 279.1 | 117.1 | 2132 | 2492 |  |  |
| 15 | 281.8 | 117.3 | 2116 | 2475 |  |  |
| 16 | 284.4 | 117.5 | 2099 | 2458 |  |  |
| 17 | 287.0 | 117.7 | 2974 | 2442 | 643.9 liq. |  |
| 18 | 289.9 | 117.9 | 2936 | 2673 |  |  |
| BED | 292.0 | 118.1 | 2891 | 2635 |  |  |
| 50 | 293.9 | 118.3 | 2846 | 2590 |  |  |
|  | 295.6 | 118.5 | 2802 | 2545 |  |  |
|  | 297.2 | 118.7 | 2758 | 2501 |  |  |
|  | 298.6 | 118.9 | 2715 | 2457 |  |  |
|  | 299.8 | 119.1 | 2671 | 2413 |  |  |
|  | 301.0 | 119.3 | 2628 | 2370 |  |  |
|  | 302.1 | 119.5 | 2585 | 2327 |  |  |
|  | 303.1 | 119.7 | 2541 | 2284 |  |  |
|  | 304.0 | 119.9 | 2497 | 2240 |  |  |
|  | 305.0 | 120.1 | 2452 | 2196 |  |  |
|  | 306.0 | 120.3 | 2406 | 2151 |  |  |
|  | 307.2 | 120.5 | 2358 | 2105 |  |  |
| 32 | 308.6 | 120.7 | 1981 | 2056 |  | 326.2 liq. |
| BED | 310.2 | 120.9 | 1968 | 2006 |  |  |
| 72 | 312.2 | 121.1 | 1955 | 1993 |  |  |
|  | 314.4 | 121.3 | 1941 | 1980 |  |  |
|  | 316.7 | 121.5 | 1928 | 1966 |  |  |
|  | 319.1 | 121.7 | 1916 | 1953 |  |  |
|  | 321.4 | 121.9 | 1906 | 1941 |  |  |
|  | 323.5 | 122.1 | 1899 | 1931 |  |  |
|  | 325.4 | 122.3 | 1894 | 1924 |  |  |
|  | 326.9 | 122.5 | 1890 | 1919 |  |  |
|  | 328.1 | 122.7 | 1888 | 1915 |  |  |
|  | 329.0 | 122.9 | 1887 | 1913 |  |  |
|  | 329.7 | 123.1 | 1886 | 1912 |  |  |
|  | 330.2 | 123.3 | 1886 | 1911 |  |  |
|  | 330.7 | 123.5 | 1886 | 1911 |  |  |

TABLE 3-continued

| TRAY | TEMP °F. | PRESSURE PSIA | LIQUID LBM/H | VAPOR LBM/H | FEED LBM/H | PRODUCT LBM/H |
|---|---|---|---|---|---|---|
| 47 | 331.0 | 123.7 | 1876 | 1911 | 108.5 vap. | |
| 48 | 338.0 | 123.9 | 1925 | 1792 | | |
| 49R | 338.3 | 124.1 | | 1841 | | 83.4 liq. |

The invention claimed is:

1. A process for the hydrogenation of olefins, diolefins and acetylenes in a hydrocarbon stream comprising the steps of:

feeding hydrogen and a stream comprising a mixture of hydrocarbons having a range of carbon numbers containing olefins, diolefins and acetylene to a first distillation column reactor below a first primary bed and first secondary bed of hydrogenation catalyst wherein a first hydrocarbon having a carbon number less than the highest carbon number in said range is boiled upward into said first primary bed along with the hydrocarbons having a lower carbon number than said first hydrocarbon, said first hydrocarbon being concentrated in said first primary bed and designated the first key component;

hydrogenating substantially all of the diolefins and acetylenes contained within said first key component to monoolefins in said first primary bed and a portion of the diolefins and acetylenes contained within the hydrocarbons having a lower carbon number than said first key component to produce a diolefin depleted stream containing olefins;

hydrogenating substantially all of the remainder of the olefins and acetylenes contained within said hydrocarbons having a lower carbon number than said first hydrocarbon to monoolefins in said first secondary bed;

separating hydrocarbons having carbon numbers higher than said first key component from the diolefin and acetylene depleted stream containing the first key component and hydrocarbons having a lower carbon number than said key component;

feeding the diolefin and acetylene depleted stream containing olefins to a second distillation column reactor above a second primary bed and a second secondary bed of hydrogenation catalyst wherein a second hydrocarbon having a carbon number higher than said first key component is concentrated within said second primary bed while said first key component is concentrated below said second primary bed, said secondary hydrocarbon being designated the second key component;

feeding hydrogen to said second distillation column reactor below the second secondary bed of hydrogenation catalyst; and hydrogenating substantially all of the olefins contained within said second key component and a portion of the olefins contained within the first key components to alkanes within said second primary bed; and hydrogenating substantially all of the remaining olefins contained within said first key component to alkanes within said second secondary bed.

2. A process for the hydrogenation of olefins, diolefins and acetylenes in a $C_5$ and heavier hydrocarbon stream comprising:

feeding hydrogen and a stream comprising a $C_5$ and heavier mixture of hydrocarbons containing olefins, diolefins and acetylene to a first distillation column reactor below a first primary bed and first secondary bed of hydrogenation catalyst wherein the $C_6$ and lighter hydrocarbons are boiled up into said first primary bed and said $C_6$ hydrocarbons are concentrated in said first primary bed and said $C_5$ hydrocarbons are concentrated in said first secondary bed;

hydrogenating substantially all of the $C_6$ diolefins and acetylenes in said first primary bed and a portion of the $C_5$ diolefins and acetylenes to produce monoolefins;

hydrogenating substantially all of the remainder of the $C_5$ acetylenes and diolefins to monoolefins in said first secondary bed;

separating the $C_7$ and heavier hydrocarbon from the $C_6$ and lighter hydrocarbons;

feeding the $C_6$ and lighter hydrocarbons containing olefins to a second distillation column reactor above a second primary bed and a second secondary bed of hydrogenation catalyst wherein the $C_5$ hydrocarbons are concentrated within said second primary bed while said $C_6$ hydrocarbons are concentrated in said second secondary bed;

feeding hydrogen to said second distillation column reactor below the second secondary bed of hydrogenation catalyst; and hydrogenating substantially all of the $C_5$ olefins contained and a portion of the $C_6$ olefins to alkanes within said second primary bed; and hydrogenating substantially all of the remaining $C_6$ olefins to alkanes within said second secondary bed.

3. The process according to claim 2 wherein a portion of the acetylene and diolefin depleted $C_6$ hydrocarbons are removed as a side draw between said first primary and said first secondary beds and the remainder of said acetylene and diolefin depleted $C_6$ hydrocarbons are removed as overheads along with the acetylene and diolefins depleted $C_5$ hydrocarbons.

4. The process according to claim 3 wherein a portion of said overheads are condensed and returned to said first distillation column reactor as reflux.

5. The process according to claim 4 wherein a portion of said side draw is condensed and a portion of said condensed side draw is combined with a portion of said condensed overheads and returned to said first distillation column reactor as reflux.

6. The process according to claim 3 wherein said side draw is combined with said overheads as feed to said second distillation column reactor.

* * * * *